United States Patent
Park et al.

(10) Patent No.: US 11,639,920 B2
(45) Date of Patent: May 2, 2023

(54) MULTIPLE QUALITATIVE AND QUANTITATIVE HEAVY METAL ANALYSIS DEVICE IMPLEMENTED BY ROTARY PLATFORM

(71) Applicant: LG Chem, Ltd., Seoul (KR)

(72) Inventors: Byung Hyun Park, Daejeon (KR);
Byoung Hyoun Kim, Daejeon (KR);
Su Youn Han, Daejeon (KR);
Gyeongjin Lee, Daejeon (KR)

(73) Assignee: LG Chem, Ltd.

( * ) Notice: Subject to any disclaimer, the term of this patent is extended or adjusted under 35 U.S.C. 154(b) by 318 days.

(21) Appl. No.: 16/771,534

(22) PCT Filed: Aug. 19, 2019

(86) PCT No.: PCT/KR2019/010490
§ 371 (c)(1),
(2) Date: Jun. 10, 2020

(87) PCT Pub. No.: WO2020/045872
PCT Pub. Date: Mar. 5, 2020

(65) Prior Publication Data
US 2021/0172924 A1    Jun. 10, 2021

(30) Foreign Application Priority Data

Aug. 30, 2018 (KR) .......... 10-2018-0102651
Jul. 10, 2019 (KR) .......... 10-2019-0082963

(51) Int. Cl.
*G01N 33/205*    (2019.01)
*G01N 35/02*    (2006.01)
(Continued)

(52) U.S. Cl.
CPC ......... *G01N 33/205* (2019.01); *G01N 33/202* (2019.01); *G01N 33/208* (2019.01); *G01N 35/02* (2013.01); *G01N 2035/0449* (2013.01)

(58) Field of Classification Search
CPC .............. G01N 33/205; G01N 35/02; G01N 2035/0449
See application file for complete search history.

(56) References Cited

U.S. PATENT DOCUMENTS

| 5,496,736 A | 3/1996 | Stone |
| 2003/0092008 A1* | 5/2003 | Bell ................. G01N 33/54346 436/523 |

(Continued)

FOREIGN PATENT DOCUMENTS

| CN | 101008643 B | * | 3/2013 | |
| CN | 102509790 B | * | 2/2014 | ............ H01M 4/366 |

(Continued)

OTHER PUBLICATIONS

CN-102509790-B—English (Year: 2014).*
(Continued)

*Primary Examiner* — Daniel S Larkin
*Assistant Examiner* — Fatemeh Esfandiari Nia
(74) *Attorney, Agent, or Firm* — Lerner David LLP

(57) ABSTRACT

A qualitative and quantitative heavy metal analysis device and, more particularly, a qualitative and quantitative heavy metal analysis device implemented by a rotary platform are provided. The rotary platform device includes a main injection part which is positioned near a rotating shaft of a rotary platform, wherein the main injection part is configured to receive a fluid sample containing heavy metals, a pH adjusting part configured to adjust pH of the fluid sample, a detecting part coated with a chelating agent configured to initiate a color reaction with heavy metals in the fluid sample (Continued)

US 11,639,920 B2

Page 2 by spreading the pH-adjusted fluid sample into the detecting part, and a ruler for measuring a spreading distance of the color reaction, wherein the fluid sample moves from the main injection part through the pH adjusting part to the detecting part by a rotation of the rotary platform device.

14 Claims, 13 Drawing Sheets

(51) Int. Cl.
  *G01N 35/04* (2006.01)
  *G01N 33/202* (2019.01)
  *G01N 33/208* (2019.01)

(56) References Cited

U.S. PATENT DOCUMENTS

| | | | |
|---|---|---|---|
| 2003/0224395 A1* | 12/2003 | Jovanovich | C12Q 1/6806 506/26 |
| 2008/0166821 A1* | 7/2008 | Oyamada | G01N 33/542 436/536 |
| 2008/0237151 A1 | 10/2008 | Cho et al. | |
| 2010/0297659 A1 | 11/2010 | Yoo | |
| 2011/0263030 A1 | 10/2011 | Kim | |
| 2012/0135396 A1* | 5/2012 | McDevitt | G01N 21/6454 435/5 |
| 2014/0287524 A1 | 9/2014 | Lee et al. | |
| 2015/0238955 A1 | 8/2015 | Lee et al. | |
| 2016/0236195 A1* | 8/2016 | Daridon | B01L 3/502761 |
| 2016/0289669 A1 | 10/2016 | Fan et al. | |
| 2017/0219614 A1* | 8/2017 | Cook | B01L 3/50851 |
| 2018/0010990 A1* | 1/2018 | Cherubini | G01N 35/00584 |
| 2020/0033240 A1 | 1/2020 | Cherubini et al. | |
| 2020/0141962 A1 | 5/2020 | Park et al. | |
| 2020/0191808 A1 | 6/2020 | Cook et al. | |

FOREIGN PATENT DOCUMENTS

| | | | |
|---|---|---|---|
| CN | 106573256 A | | 4/2017 |
| CN | 107076770 A | | 8/2017 |
| EP | 1444518 A1 | | 8/2004 |
| JP | H11124682 A | | 5/1999 |
| JP | 2007278741 A | | 10/2007 |
| KR | 20080089835 A | | 10/2008 |
| KR | 100883658 B1 | * | 2/2009 |
| KR | 100883658 B1 | | 2/2009 |
| KR | 20110079570 A | | 7/2011 |
| KR | 20110088746 A | | 8/2011 |
| KR | 20130000009 A | | 1/2013 |
| KR | 101256474 B1 | * | 4/2013 |
| KR | 101256474 B1 | | 4/2013 |
| KR | 20140115912 A | | 10/2014 |
| KR | 20150101307 A | | 9/2015 |
| KR | 20190058249 A | | 5/2019 |
| WO | 2016118915 A1 | | 7/2016 |
| WO | 2017210199 A1 | | 12/2017 |

OTHER PUBLICATIONS

CN-101008643-B—English (Year: 2013).*
Extended European Search Report including Written Opinion for EP19855812.4 dated Jul. 1, 2020; 10 pages.
Atwe, et al., "A novel microfluidic switch for pH control using Chitosan based hydrogels." Microsystem Technol, vol. 20, Issue 7, published online Feb. 21, 2014, pp. 1373-1381.
Chang, et al., "Modified nanoporous membranes on centrifungal microfluidic platforms for detecting heavy metal ions." Materials Research Innovations, vol. 18, Suppl. 2, published online May 30, 2014, pp. 685-690.
International Search Report from Application No. PCT/KR2019/ 010490 dated Nov. 29, 2019, 2 pages.
Search Report dated Jan. 17, 2023 from the Office Action for Chinese Application No. 201980006087.4 issued Jan. 20, 2023, pp. 1-3.

* cited by examiner

[Fig. 1]
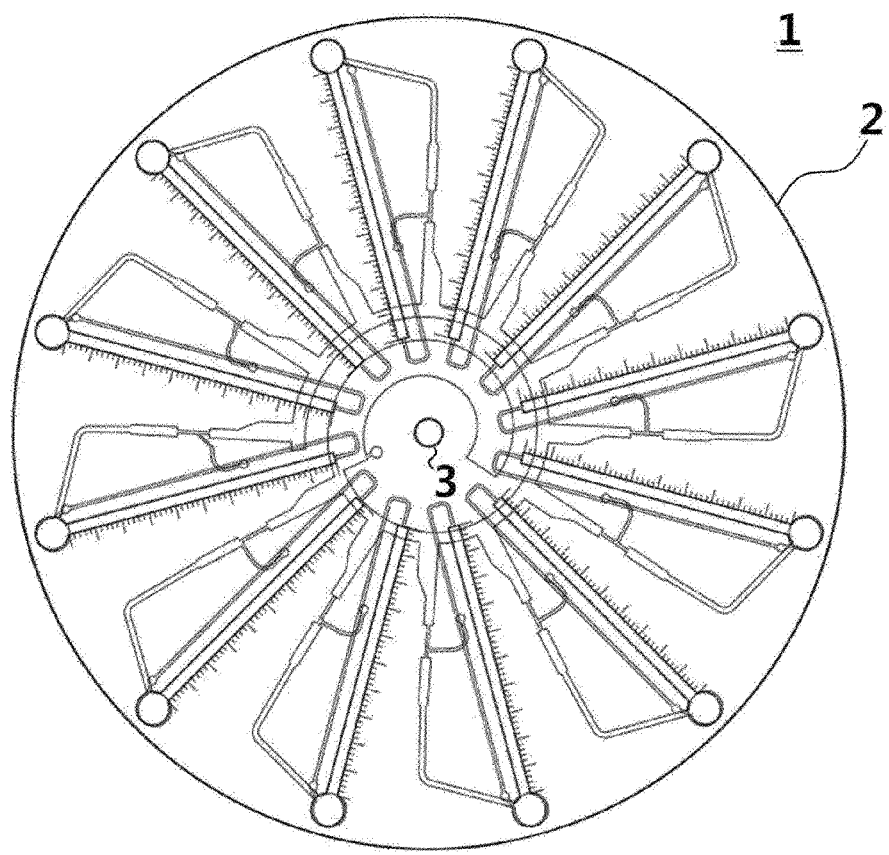

[Fig. 2a]
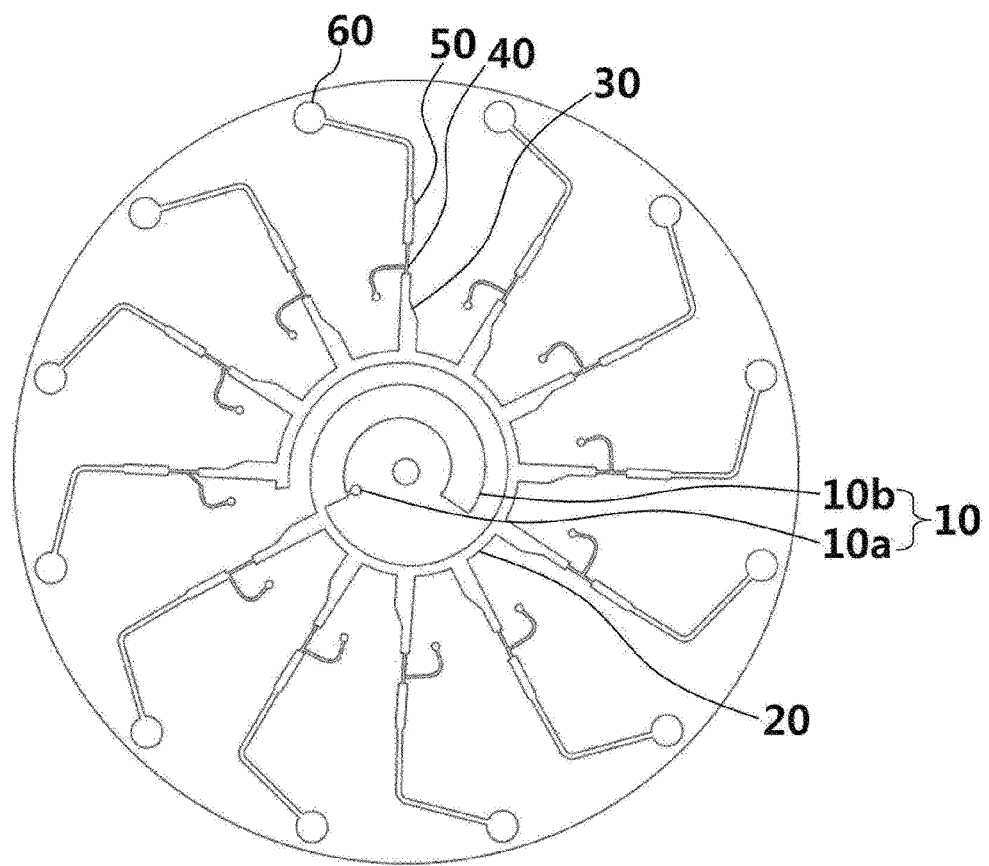

[Fig. 2b]
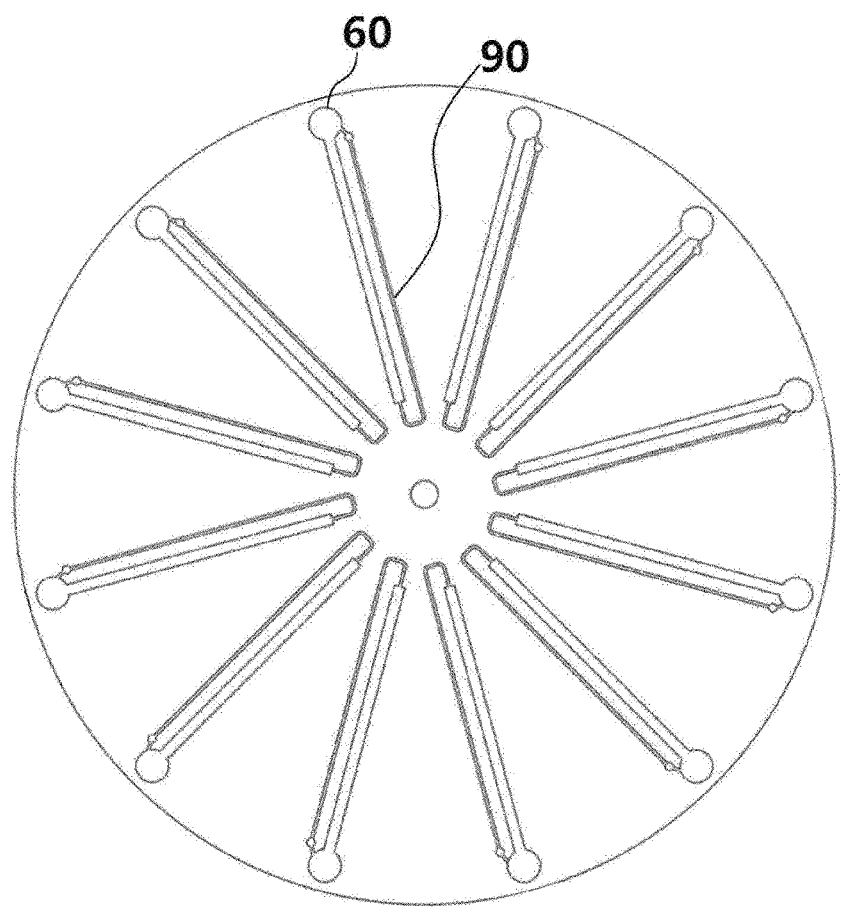

[Fig. 2c]
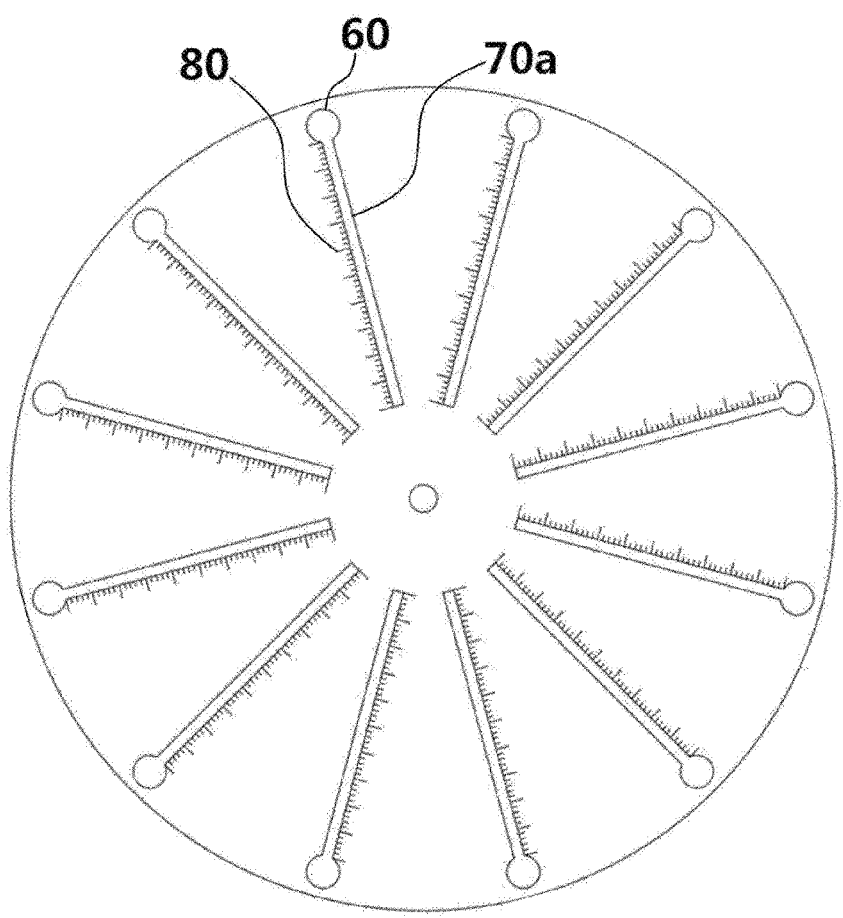

[Fig. 2d]
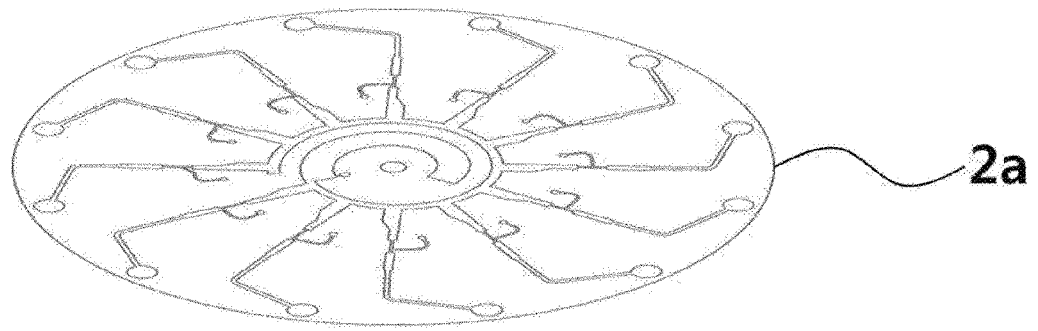 2a
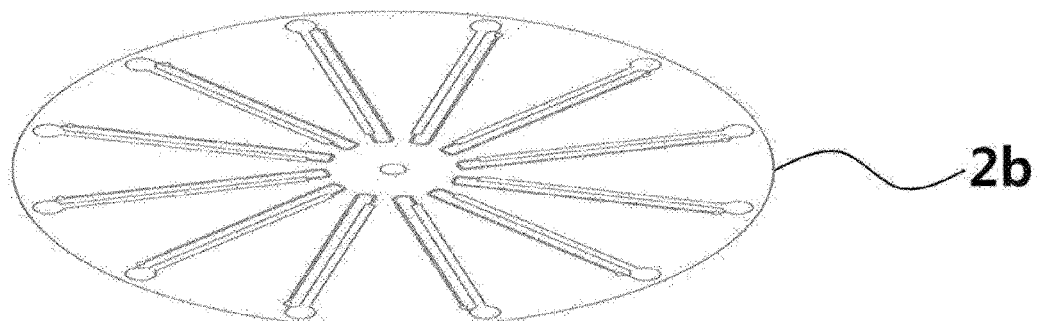 2b
70
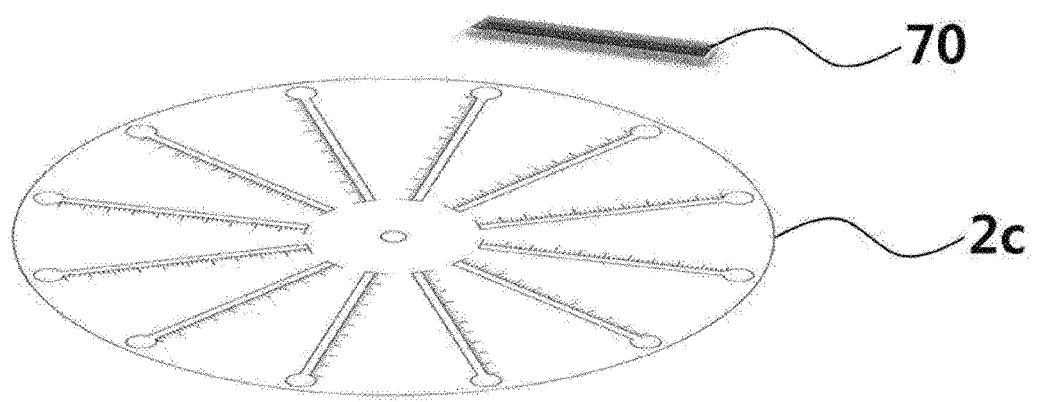 2c

[Fig. 4]
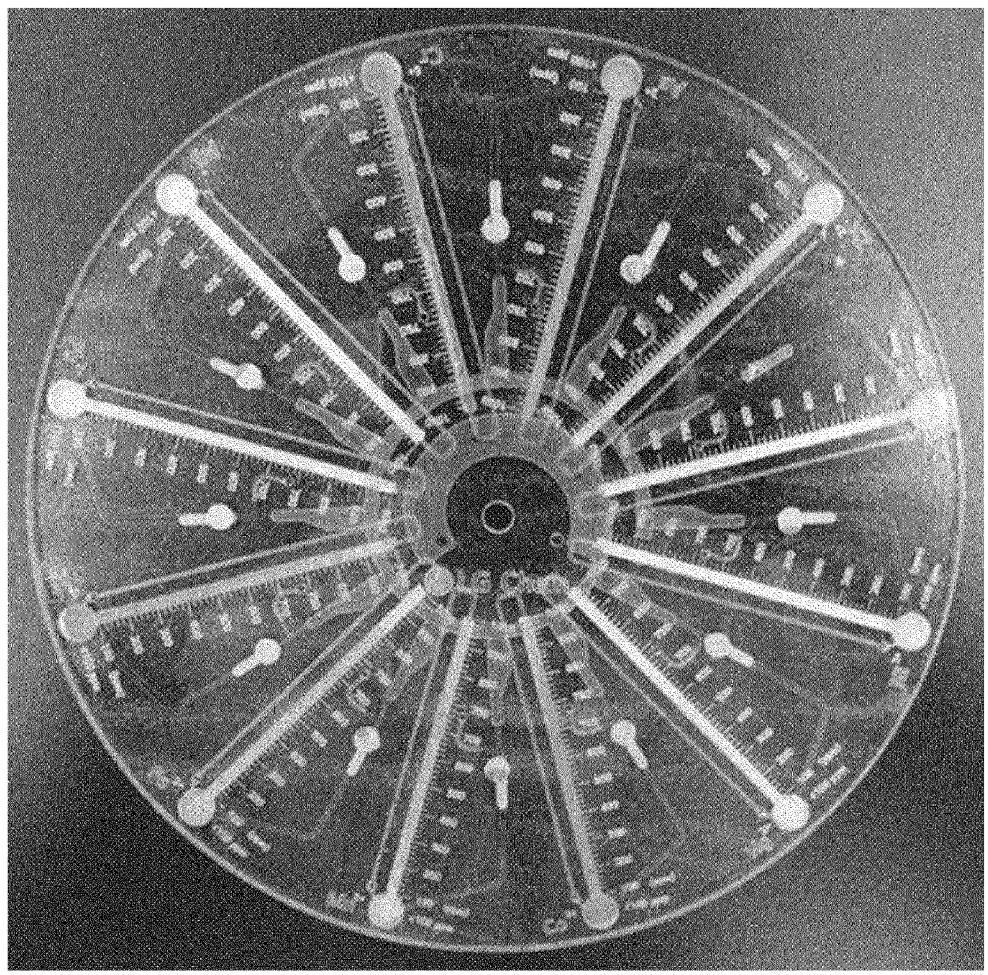

[Fig. 6]
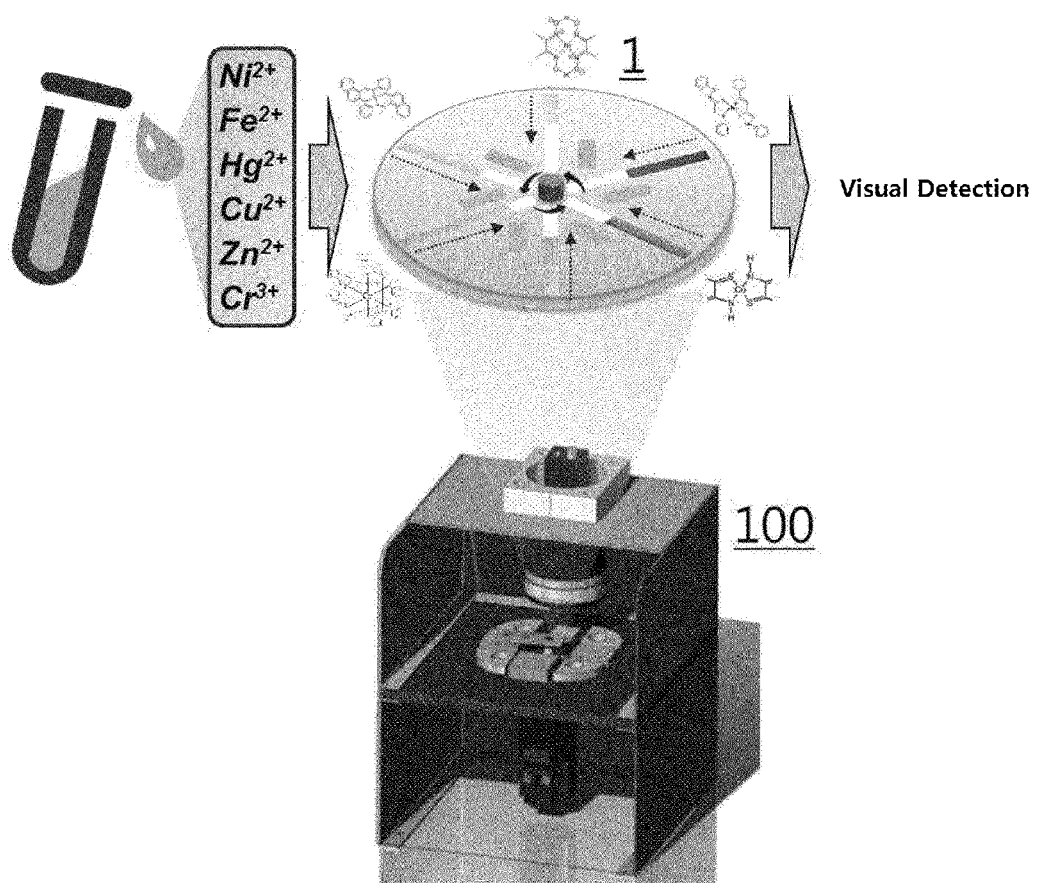

MULTIPLE QUALITATIVE AND QUANTITATIVE HEAVY METAL ANALYSIS DEVICE IMPLEMENTED BY ROTARY PLATFORM

CROSS-REFERENCE TO RELATED APPLICATIONS

The present application is a national phase entry under 35 U.S.C. § 371 of International Application No. PCT/KR2019/010490 filed Aug. 19, 2019 which claims priority from Korean Patent Application Nos. 10-2018-0102651, filed on Aug. 30, 2018 and 10-2019-0082963, filed on Jul. 10, 2019, the entire disclosures of which are incorporated herein by reference.

BACKGROUND OF THE INVENTION

Field of the Invention

The present invention relates to a rotary platform device for qualitative and quantitative analysis of multiple heavy metals, and more particularly, to qualitative and quantitative analysis devices for heavy metal samples in the form of rotary disc.

Description of the Related Art

In general, the most common detection method of heavy metals is spectroscopic analysis such as inductively coupled plasma mass spectrometry or atomic absorption and emission spectrophotometer. Mass and spectroscopy-based detection methods for heavy metals have accuracy and high detection limit, but they require expensive and skilled analytical techniques, making it difficult to perform heavy metal analysis on site quickly and simply.

SUMMARY OF THE INVENTION

In order to replace the expensive mass and spectroscopy-based analysis device of heavy metals, it is necessary to develop an economical and inexpensive color development-based analysis system of heavy metals, and to develop a compact analysis system that can be conveniently applied in the field. In addition, the development of a system is required which is capable of performing quantitative analysis as well as qualitative analysis of heavy metals while reducing the analysis time through the simultaneous detection of multiple heavy metals.

The rotary platform device for qualitative and quantitative analysis device according to the present invention may comprise:

a main injection part which is positioned near a rotating shaft of the rotary platform and through which a fluid sample containing heavy metals is injected;

a pH adjusting part for adjusting pH of the injected sample;

a detecting part coated with a chelating agent capable of causing color reaction with heavy metals in the sample by spreading the pH-adjusted sample; and a ruler for measuring the spreading distance of the color reaction;

wherein the sample may move from the main injection part through the pH adjusting part to the detecting part by controlling the rotation of the device, and wherein the color reaction of the heavy metals in the detecting part enables quantitative analysis and measuring the spreading distance of the color reaction enables qualitative analysis.

Effect of the Invention

According to the qualitative and quantitative analysis device according to one embodiment of the present invention, it is possible to increase detection limit of heavy metals by automated control of fluid and by adjusting rotational force and capillary force. It is possible to improve detection limit of heavy metal ions by control of rotational force. That is, it is possible to improve detection limit by adjusting color reaction time and color development area by adjusting centrifugal force and capillary force by control of rotation.

In addition, according to the qualitative and quantitative analysis device according to an embodiment of the present invention, qualitative analysis and quantitative analysis of a plurality of heavy metals can be performed in a single device. According to the present invention, it is possible to achieve economical and rapid qualitative/quantitative analysis of multiple heavy metals. It is more economical and can reduce the time required for analysis, compared to conventional expensive spectroscopic or mass spectrometry-based detecting device of heavy metals. In addition, the configuration for qualitative analysis and the configuration for quantitative analysis are integrated into one miniaturized device, which can be quickly and conveniently applied in the field requiring qualitative/quantitative analysis of heavy metals.

In addition, since each component such as a pH adjusting part, a detecting part, and the like are patterned in one device, it is easy to manufacture a qualitative and quantitative analysis device.

In addition, according to the qualitative and quantitative analysis device according to an embodiment of the present invention, by providing an air circulation channel, it is possible to prevent moisture condensation of the detecting part when the fluid sample is spread in the detecting part so that color development can be easily identified and errors of analysis can be minimized, and it is possible to move a fluid sample more uniformly when the fluid sample is spread in the detecting part so that color reaction between chelating agent coated one the detecting part and heavy metals of the sample can more uniformly occur.

BRIEF DESCRIPTION OF THE DRAWINGS

FIG. 1 shows a rotary platform device for qualitative and quantitative analysis according to one embodiment of the invention.

FIGS. 2a to 2d show each layer of the rotary platform of the qualitative and quantitative analysis device of FIG. 1.

FIG. 4 shows a photograph of a case where color reaction occurs when a sample is spread on the rotary platform of the qualitative and quantitative analysis device of FIG. 1.

FIG. 6 shows a qualitative and quantitative analysis system in which the qualitative and quantitative analysis device of FIG. 1 can be mounted and rotated.

DETAILED DESCRIPTION OF THE INVENTION

Figure 3:
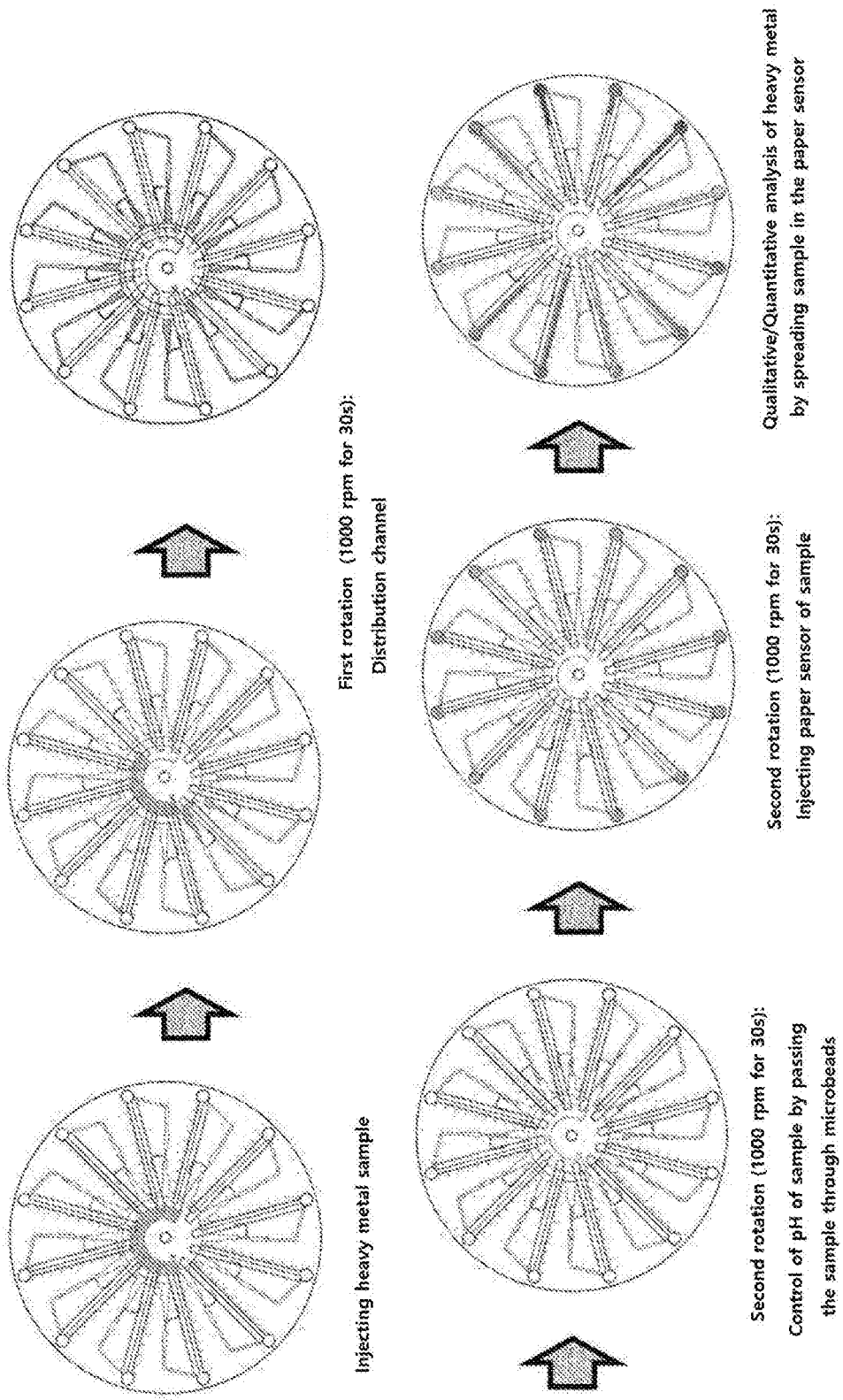
FIG. 3 shows the driving process of the rotary platform of the qualitative and quantitative analysis device of FIG. 1.
Figure 5A:
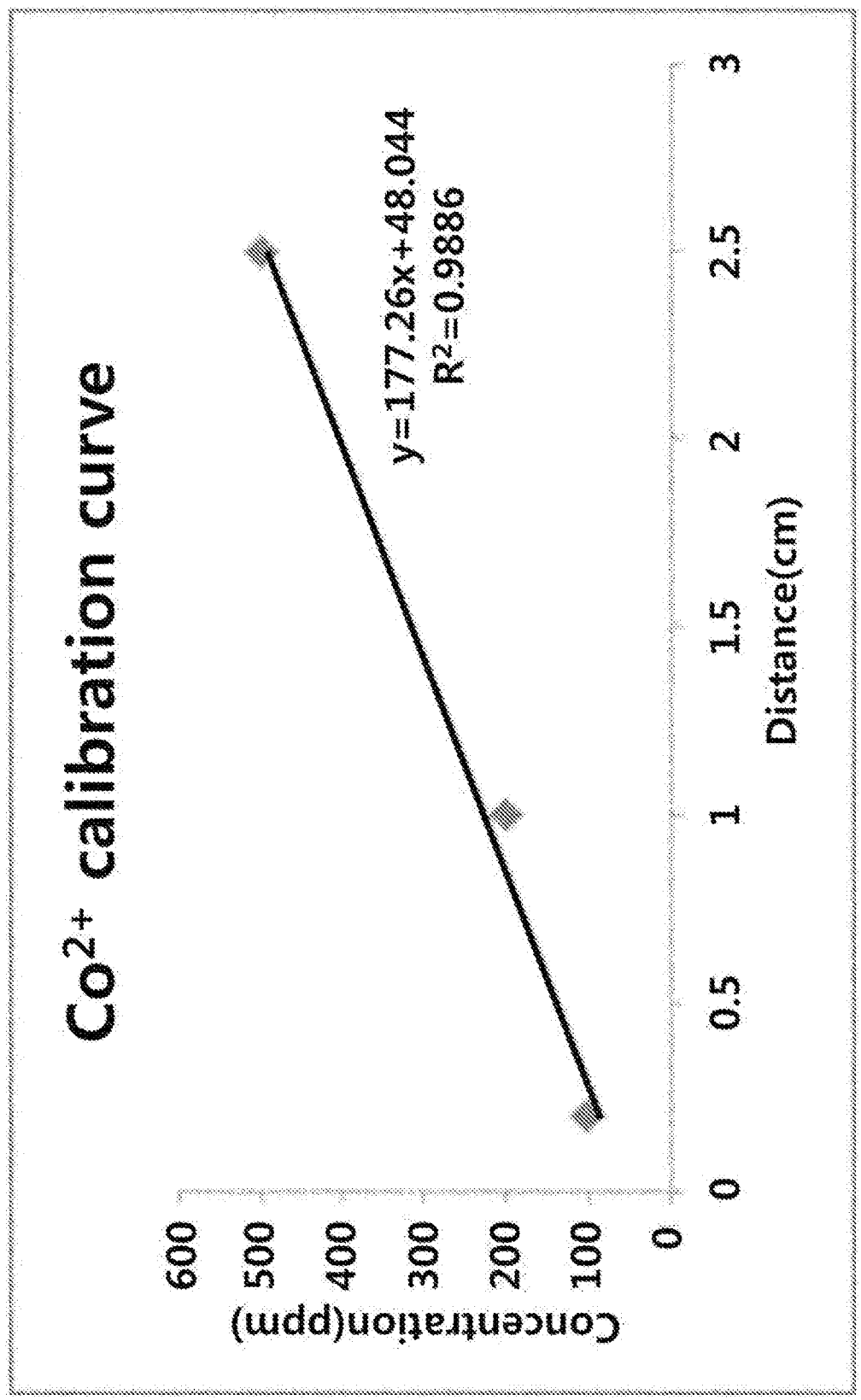
FIGS. 5a to 5e show calibration curve for spreading distance of color development according to heavy metal concentration.
Figure 5B:
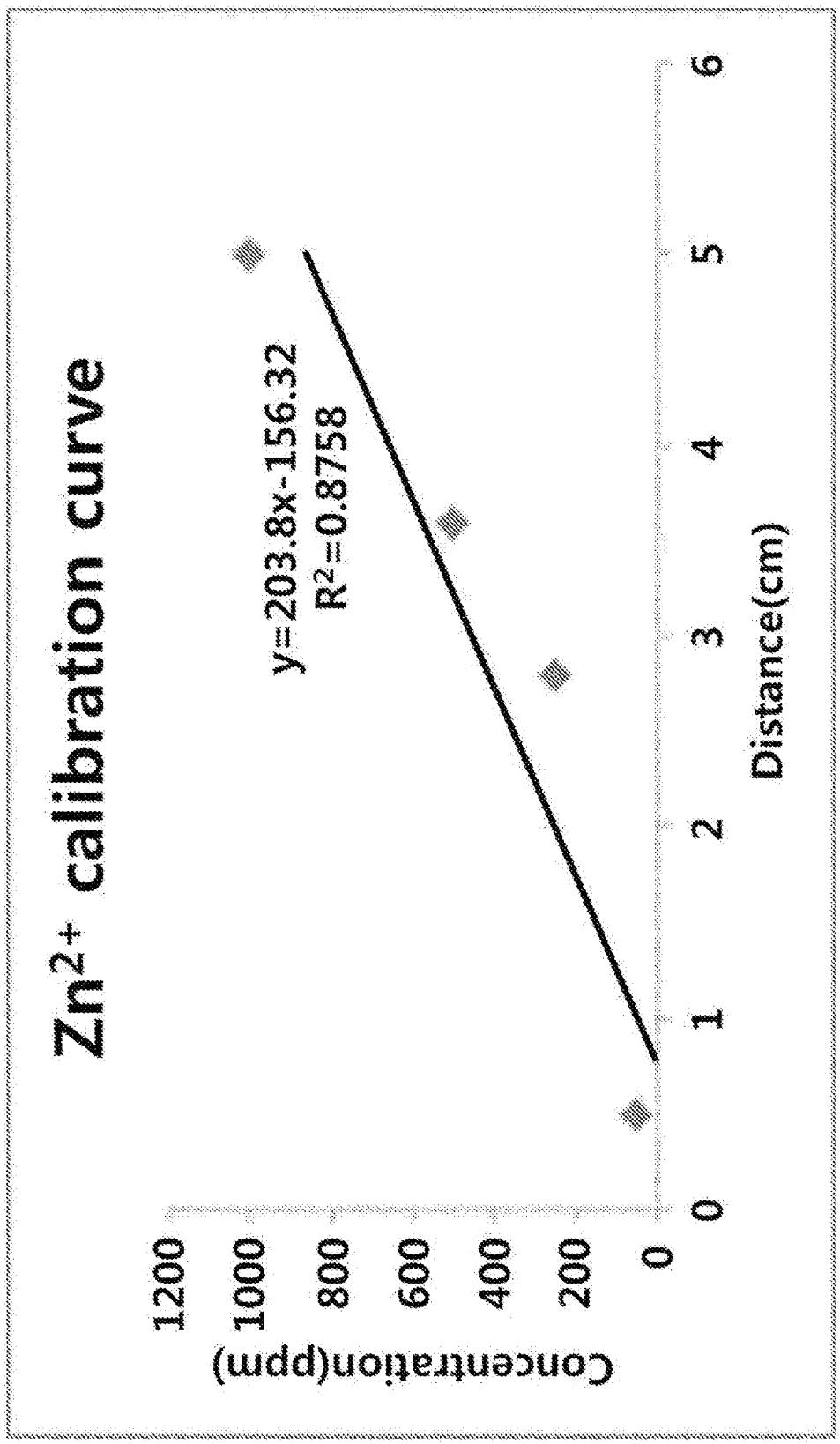
Figure 5C:
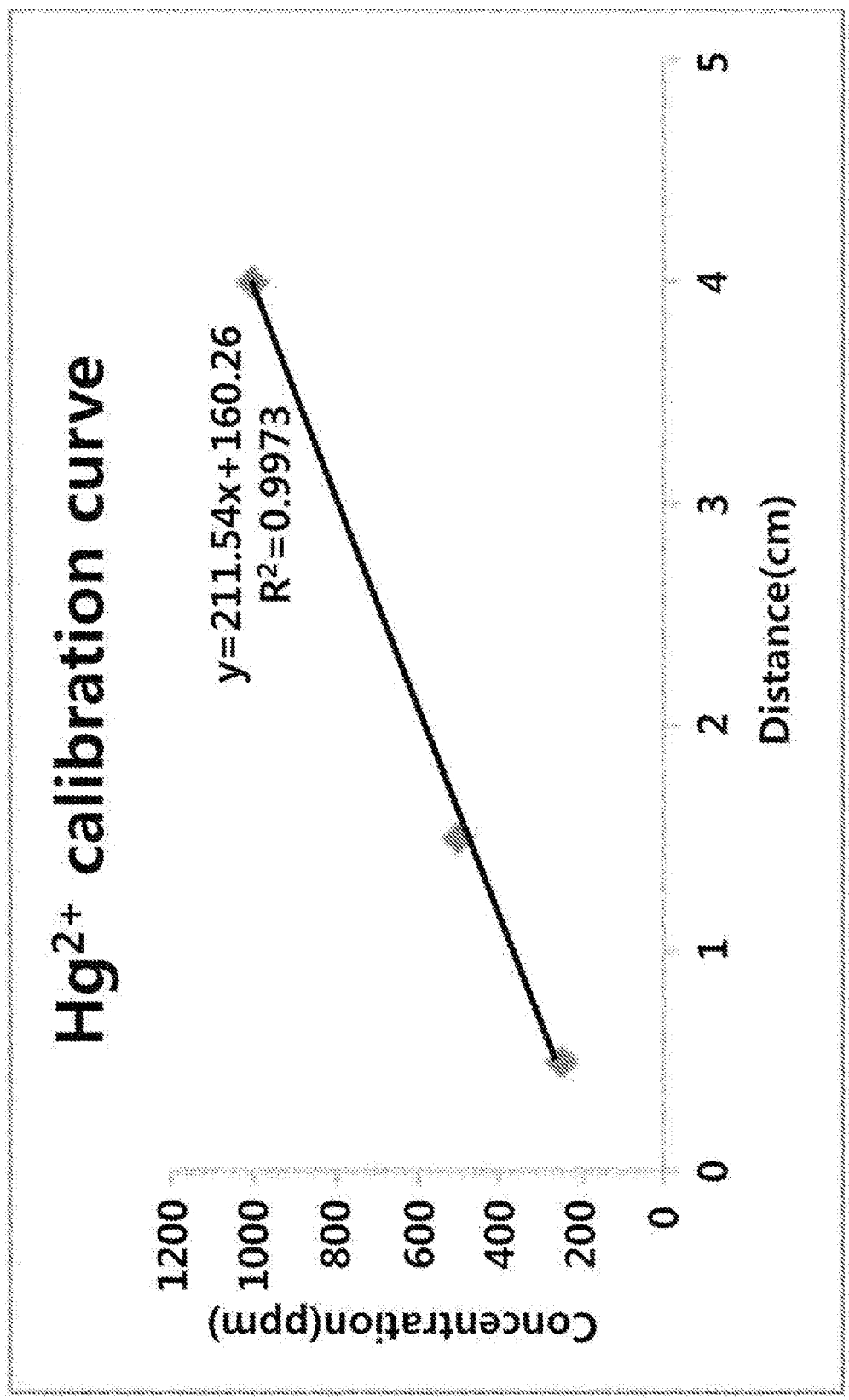
Figure 5D:
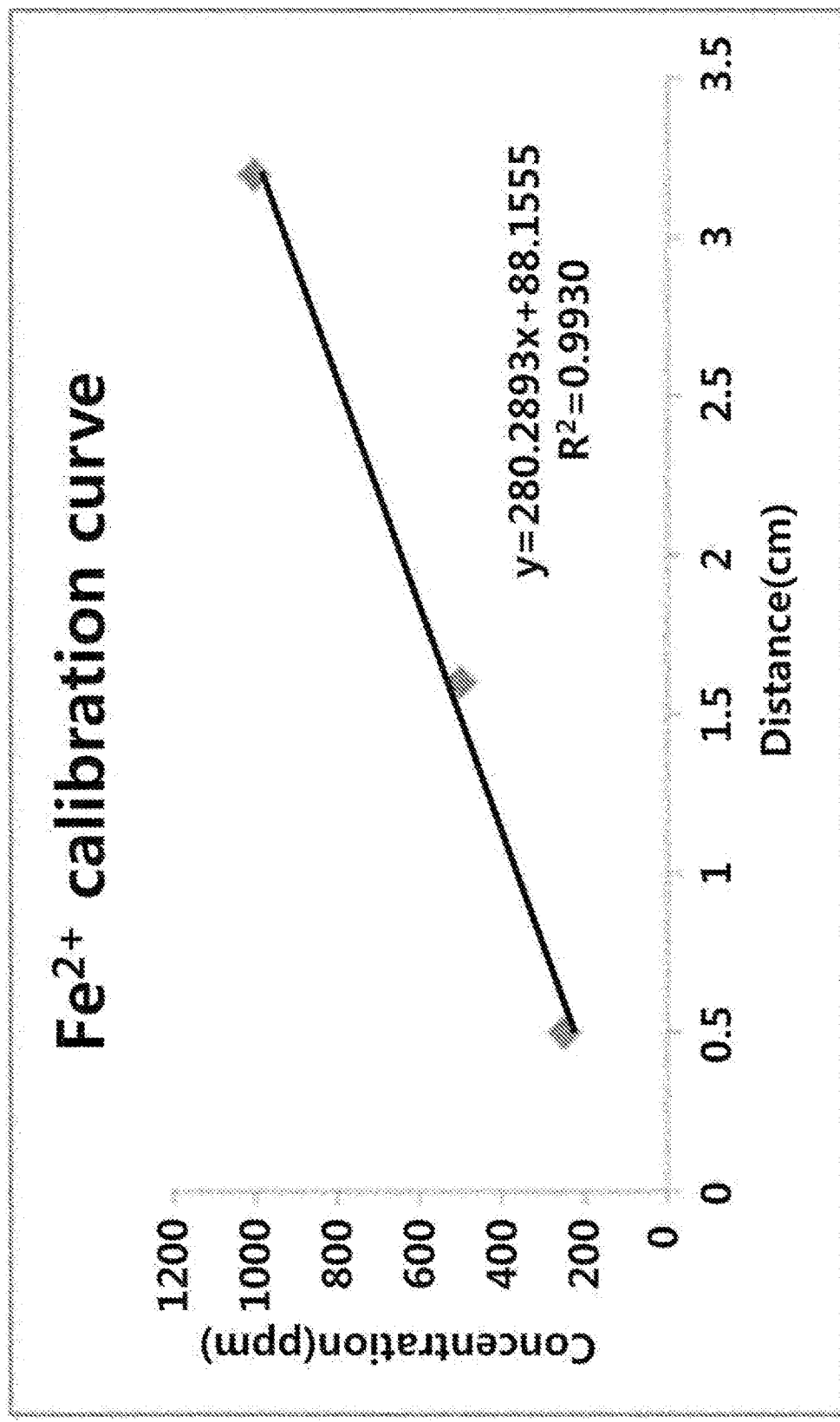
Figure 5E:
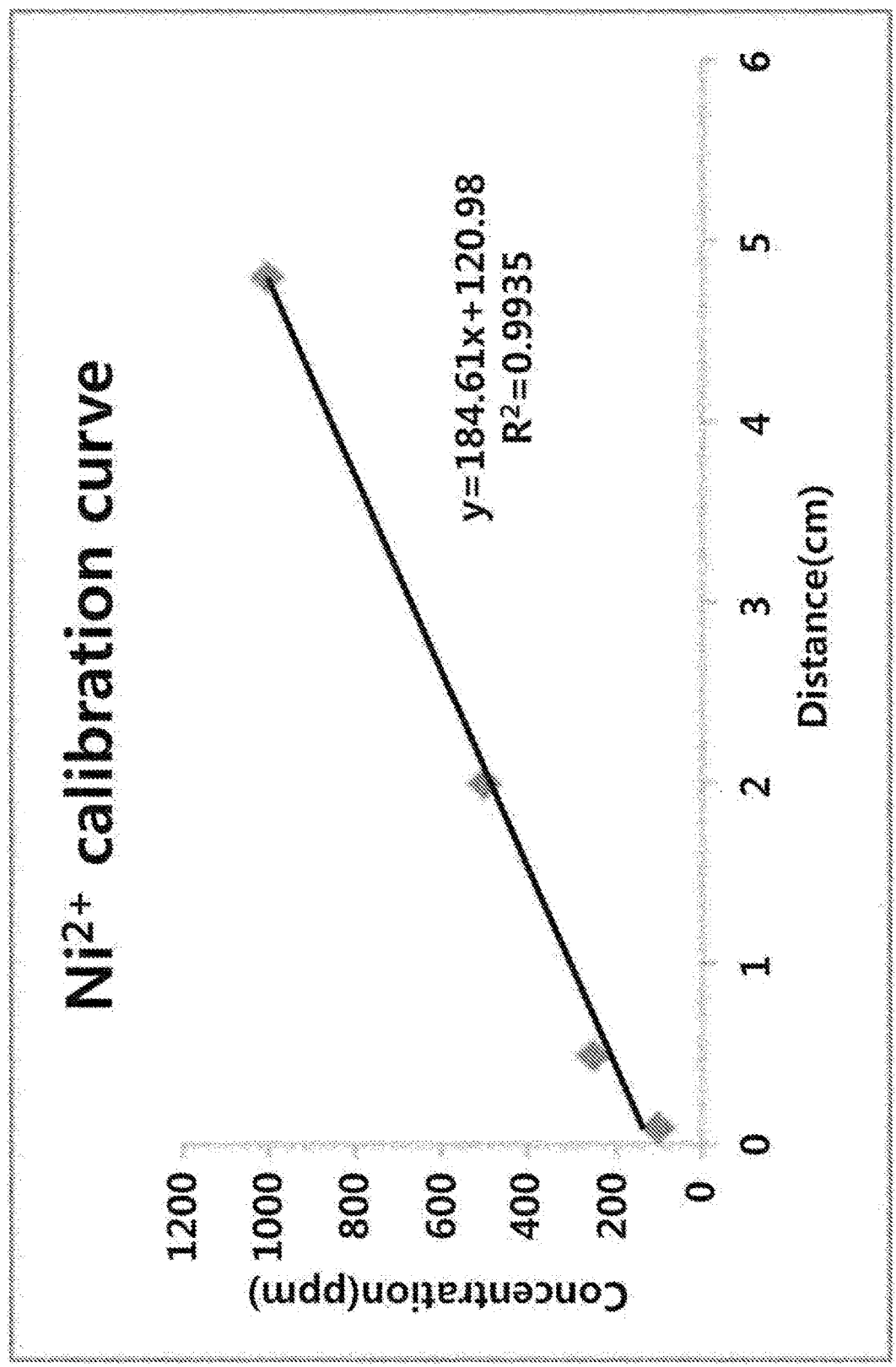

The rotary platform device for qualitative and quantitative analysis according to the present invention may comprise:

a main injection part which is positioned near a rotating shaft of the rotary platform and through which a fluid sample containing heavy metals is injected;

a pH adjusting part for adjusting pH of the injected sample;

a detecting part coated with a chelating agent capable of causing color reaction with heavy metals in the sample by spreading the pH-adjusted sample; and a ruler for measuring the spreading distance of the color reaction;

wherein the sample may move from the main injection part through the pH adjusting part to the detecting part by controlling the rotation of the device, and wherein the quantitative analysis is achieved by the color reaction of the heavy metals in the detecting part and the qualitative analysis is achieved by measuring the spreading distance of the color reaction.

In addition, in the rotary platform device for qualitative and quantitative analysis according to the present invention, the pH adjusting part may be filled with microbeads and the surface of the microbeads may be coated with a salt, so that the injected sample can be adjusted to have a desired pH in the channel.

In addition, the rotary platform device for qualitative and quantitative analysis according to the present invention may further comprise a reservoir region connecting the pH adjusting part and the detecting part, wherein one end of the detecting part may be accommodated in the reservoir region.

In addition, in the rotary platform device for qualitative and quantitative analysis according to the present invention, the pH adjusting part, the detecting part and the ruler may be provided in plurality, and each of the pH adjusting part, the detecting part and the ruler may be radially symmetrically disposed on the rotary platform.

In addition, the rotary platform device for qualitative and quantitative analysis according to the present invention may further comprise a main passage part connected to an end of the main injection part; and a plurality of sample distribution channels connected to the main passage part, wherein each of the sample distribution channels may have a shape extending radially symmetrically from the main passage part.

In addition, in the rotary platform device for qualitative and quantitative analysis according to the present invention, the main injection part may comprise a sample reservoir for storing the injected sample before distributing to each of the sample distribution channels, and the shape in which the sample reservoir and the main passage part may be a spiral shape.

In addition, the rotary platform device for qualitative and quantitative analysis according to the present invention may further comprise a plurality of on/off valves, each of which is provided between each of the sample distribution channels and each of the pH adjusting part, and the on/off valve may be opened by rotational force of the rotary platform so that the sample accommodated in the sample distribution channel can pass through the pH adjusting part.

In addition, the rotary platform device for qualitative and quantitative analysis according to the present invention may further comprise a plurality of air circulation channels, each of which connects each of the reservoir regions and other end of each of the detecting parts, and the air circulation channel may increase the evaporation rate of the fluid sample in the detecting part and prevent moisture condensation in the detecting part.

In addition, in the rotary platform device for qualitative and quantitative analysis according to the present invention, the rotary platform may be comprised of:

a top layer including the main injection part, the main passage part, the sample distribution channel, the on/off valve, the pH adjusting part and the reservoir region;

a middle layer including the air circulation channel and the reservoir region and having a shape in which a portion corresponding to the detecting part is opened; and a bottom layer including the reservoir region and the ruler and having a space in which the detecting part is inserted.

In addition, in the rotary platform device for qualitative and quantitative analysis according to the present invention, the sample may be adjusted to have a pH that is optimized to occur the reaction between the heavy metals contained in the sample and the chelating agent while passing through the microbeads filled in the pH adjusting part.

In addition, in the rotary platform device for qualitative and quantitative analysis according to the present invention, the heavy metals contained in the sample may be $Fe^{2+}$, $Ni^{2+}$, $Cu^{2+}$, $Cr^{6+}$, $Hg^{2+}$, $As^{2+}$, $Zn^{2+}$, $Mn^{2+}$, $Cd^{2+}$, $Pb^{2+}$, $Co^{2+}$, or $Ag^+$.

In addition, in the rotary platform device for qualitative and quantitative analysis according to the present invention, the chelating agent applied on the detecting part in advance may comprise bathophenanthroline (Bphen), dimethylglyoxime (DMG), dithiooxamide (DTO), diphenylcarbazide (DPC), dithizone (DTZ), Eriochrome Black T (EBT), or 1-(2-pyridylazo)-2-naphthol (PAN).

In addition, in the rotary platform device for qualitative and quantitative analysis according to the present invention, the rotation of the device may be controlled in such a way of:

firstly rotating and then stopping the device so that the sample injected into the main injection moves to the sample distribution channel;

secondly rotating the device so that the sample moved to the sample distribution channel move through pH adjusting part to the reservoir region; and stopping the device so that the sample moved to the reservoir region spreads into the detecting part.

In addition, in the rotary platform device for qualitative and quantitative analysis according to the present invention, the first rotation and the second rotation may be performed at 1000 RPM for 30 seconds, respectively.

Hereinafter, a rotary platform device for qualitative and quantitative analysis of multiple heavy metals according to one embodiment of the present invention (hereinafter, referred to as 'qualitative and quantitative analysis device') will be described in detail. The accompanying drawings, which are included to provide a further understanding of the invention, illustrate embodiments of the invention and are not intended to limit the technical scope of the present invention.

In addition, the same or corresponding components will be denoted by the same reference numerals regardless of symbols, and redundant description thereof will be omitted. For convenience of explanation, the size and shape of each component shown may be exaggerated or reduced.

FIG. 1 shows a qualitative and quantitative analysis 1 according to one embodiment of the invention. FIGS. 2a to 2d show each layer of the rotary platform 2 of the qualitative and quantitative analysis device 1 of FIG. 1.

Referring to FIG. 1, the qualitative and quantitative analysis device 1 is implemented on a rotary platform 2. The rotary platform 2 can be, for example, of a circular disc type, the size of which may be, for example, in one embodiment, 14 cm to 16 cm in diameter, and in another embodiment, less than 25 cm in diameter. Referring to FIGS. 2a to 2d, the rotary platform 2 is consist of a top layer 2a (see FIG. 2a), a middle layer 2b (see FIG. 2b), a bottom layer (see FIG. 2c).

The qualitative and quantitative analysis device 1 includes a main injection part 10, a main passage part 20, a sample distribution channel 30, an on/off valve 40, a pH adjusting part 50, a reservoir region 60, a detecting part 70, a ruler 80, and an air circulation channel 90.

The main injection part 10 is disposed near a rotating shaft 3, and the main injection part 10, the main passage part 20, the sample distribution channel 30, an on/off valve 40, a pH adjusting part 50 and a reservoir region 60 are arranged in this order in a direction from the rotating shaft 3 to the edge of the rotary platform 2.

The sample distribution channel 30, the on/off valve 40, the pH adjusting part 50, the reservoir region 60, the detecting part 70, the ruler 80, and the air circulation channel 90 may be provided in plurality, respectively. In addition, pairs of the sample distribution channel 30, the on/off valve 40, the pH adjusting part 50, the reservoir region 60, the detecting part 70, the ruler 80, and the air circulation channel 90 may be disposed radially around the rotating shaft 3.

More specifically, the top layer 2a includes the main injection part 10, the main passage part 20, the sample distribution channel 30, the on/off valve 40, the pH adjusting part 50, and the reservoir region 60. In addition, each component of the top layer 2a may be produced through a patterning process using micro-milling. The portion where the detecting part 70 is located on the top layer 2a can be variously modified and changed, such as the lower surface of the top layer 2a may have a concave to match the shape of the detecting part 70 so that the detecting part 70 can be inserted therein. In addition, the height of the concave may be variously modified and changed according to the environment in which the present invention is actually implemented.

The middle layer 2b has a shape in which a portion corresponding to the detecting part 70 is opened, and includes an air circulation channel 90 and a reservoir region 60. The reservoir region 60 and the air circulation channel 90 may be produced through a patterning process using micro-milling.

The bottom layer 2c includes a reservoir region 60, a space 70a into which the detecting part 70 can be inserted and a patterned ruler 80. The detecting part 70 is inserted and positioned on the bottom layer 2c. On the other hand, the top layer 2a and the middle layer 2b are made of a transparent material so that the ruler and the degree of spreading of the sample in the detecting part 70 of the bottom layer 2c can be confirmed. However, the present invention is not limited to the above, and various modifications and changes are possible, such as the ruler 80 may be patterned on the top layer 2a.

The main injection part 10 includes an opening 10a into which a fluid sample containing heavy metals is injected. It also includes a sample reservoir 10b for storing the injected sample before distributing to each of the sample distribution channels 30. The amount of the sample to be injected into the main injection part 10 may be, for example, 700 μL. The sample reservoir 10b may have a shape surrounding the rotating shaft 3. The main passage part 20 is connected to an end of the sample reservoir 10b. The main passage part 20 may also have a shape surrounding the rotation shaft 3. The shape in which the sample reservoir 10b and the main passage part 20 are coupled may be a spiral shape.

The main passage part 20 is connected to the plurality of sample distribution channels 30. Each of the sample distribution channels 30 extends radially from the main passage part 20, and the plurality of sample distribution channels 30 extending from the main passage part 20 have an aliquot structure. As the qualitative and quantitative analysis device 1 rotates firstly, the sample in the main passage part 20 is distributed by the volume of each of the sample distribution channel 30 (see FIG. 3). That is, the sample injected into one main injection part is distributed through the main passage part into a plurality of sample distribution channels.

The on/off valve 40 is provided between the sample distribution channel 30 and the pH adjusting part 50. The on/off valve 40 may be, for example, a capillary valve, and may further comprise a vent hole 40a. As the qualitative and quantitative analysis device 1 rotates secondly, the on/off valve 40 is opened by the rotational force so that the sample contained in the sample distribution channel 30 passes through the pH adjusting part 50.

The sample may have the adjusted pH while passing through the pH adjusting part 50. In one embodiment, the pH adjusting part 50 may be filled with microbeads coated with a reagent that can adjust the pH of the sample. That is, the pH adjusting part 50 may include microbeads to adjust the pH of the injected sample. The surface of the microbeads is coated with a salt so that the injected sample can be adjusted to have a desired pH between pH 0 and 14 while passing through the pH adjusting part 50. In addition, by providing the microbeads in the pH adjusting part 50, the suspended matter in the sample can be filtered by the microbeads.

More specifically, the microbeads filled in the pH adjusting part 50 may have a pH at which the reaction between the heavy metal and the chelating agent occurs easily, so that the sample is adjusted to have the pH to cause a reaction between the heavy metal in the sample and the chelating agent included in the detecting part 70 while passing through the pH adjusting part 50, for example. Accordingly, the sample passed through the pH adjusting part 50 may have the same pH as the pH of the microbeads filled in the pH adjusting part 50.

The microbeads are incubated in a buffer solution to adjust to have a desired pH, followed by volatilization of a solvent component at 50° C. and in $N_2$ atmosphere to obtain microbeads with a respective desired pH. The buffer, for example, may be prepared including the reagent in Table 1. More specifically, a buffer solution having a desired pH may be prepared by adjusting a ratio of conjugate base and acid according to the following Henderson-Hasselbach equation.

$$-\log[H_3O^+] = -\log K_a - \log\frac{[HA]}{[A^-]}$$

$$pH = pK_a - \log\frac{[HA]}{[A^-]}$$

$$pH = pK_a + \log\frac{[A^-]}{[HA]}$$

wherein, $K_a$ is an acid dissociation constant, [HA] is a concentration of an acid, [A−] is a concentration of a conjugate base, and [H+] is a concentration of hydrogen ion.

In other words, the buffer solution having more than pH 0 and less than pH 14 or from pH 1 to pH 13 may be prepared by a regent combination of weak acid/strong acid, acid/base, acid/conjugate base, weak base/strong base or salt/base. In general, an acid/base regent combination and a corresponding composition ratio thereof may be used to prepare buffers with varying pH values. However, a weak acid/strong acid regent combination may primarily be used to prepare acidic buffer solutions of pH 2 to pH 4, and a weak base/strong base regent combination may primarily be used to prepare basic buffer solutions of pH 9 to pH 11, for example.

In addition, the microbeads are silica-based materials and all components of the substance in the pH buffer may be adsorbed to the microbeads. At this time, the pH of the microbeads is determined according to the composition ratio of all components of the substance except for the solvent component in each pH buffer (for example, the composition ratio of the substance of Table 1 below). When the neutral sample passes through the microbeads prepared as described above, salts adsorbed on the microbeads are eluted to change the pH of the sample, thereby controlling the sample having a desired pH.

TABLE 1

Examples of regents for preparing a pH buffer
Hydrochloric acid/Potassium chloride
Glycine/Hydrochloric acid
Potassium hydrogen phthalate/Hydrochloric acid
Citric acid/Sodium citrate
Sodium acetate/Acetic acid
Potassium hydrogen phthalate/Sodium hydroxide
Disodium hydrogen phthalate/Sodium dihydrogen orthophosphate
Dipotassium hydrogen phthalate/Potassium dihydrogen orthophosphate
Potassium dihydrogen orthophosphate/Sodium hydroxide
Barbitone sodium/Hydrochloric acid
Tris (hydroxylmethyl) aminomethane/Hydrochloric acid
Sodium tetraborate/Hydrochloric acid
Glycine/Sodium hydroxide
Sodium carbonate/Sodium hydrogen carbonate
Sodium tetraborate/Sodium hydroxide
Sodium bicarbonate/Sodium hydroxide
Sodium hydrogen orthophosphate/Sodium hydroxide
Potassium chloride/Sodium hydroxide In the Table 1, in the case of potassium hydrogen phthalate/hydrochloric acid, potassium hydrogen phthalate is used as a weak acid and hydrochloric acid is used as a strong acid. The concentrations of hydrogen ion and conjugate base from potassium hydrogen phthalate are determined by the amount of a strong acid, hydrochloric acid to be added, thereby adjusting the pH. In the manufacturing process as described above, the microbeads are sufficiently coated with salts on the surface thereof, but the microbeads may be made of silica-based material having Si—OH groups such that the salts coated on the microbeads may be sufficiently eluted into the sample when the sample passes through the pH adjusting part 50. In addition, the microbeads 100 may be any one as long as all components of the material in the pH buffer can be sufficiently adsorbed, but may have a smooth surface or a porous structure. In the case of a porous structure, the large surface area facilitates the pH control of a large volume of the sample. In addition, the diameter of the microbeads 100 may be 150 µm to 210 µm, for example. In addition, the microbeads 100 may be filled in the pH adjusting part 50 in an amount of, for example, several ten mg to several hundred mg.

The sample to be injected into the qualitative and quantitative analysis device 1 may be neutral, for example, have a pH value of 6.8 to 7.9.

As described above, when the qualitative and quantitative analysis device 1 is rotated secondly, the sample passes through the pH adjusting part 50 and moves to the reservoir region 60 disposed at the edge of the rotary platform 2 (see FIG. 3). At this time, the detecting part 70 is not developed but remains (i.e., is trapped) in the reservoir region 60 by the centrifugal force due to rotation.

When the rotation of the qualitative and quantitative analysis device 1 is stopped, the sample moved to the reservoir region 60 is spread on the detecting part 70 (see FIG. 3). One end of the detecting part 70 is connected to the reservoir region 60, and the sample accommodated in the reservoir region 60 is adjusted to have a pH at which a reaction between the heavy metal in the sample and a chelating agent included in the detecting part 70 occurs easily. At this time, one end of the detecting part 70 is accommodated in the reservoir region 60, while the sample is injected into the pH adjusting part 50 located on the top layer 2a of the rotary platform 2, passed through the reservoir region 60 which is formed throughout the top layer 2a, the middle layer 2b and the bottom layer 2c, and moved to the other end of the detecting part 70 inserted into the bottom layer 2c of the rotary platform 2, that is, the fluid sample is injected downwardly. Therefore, the fluid sample can be more uniformly spread in the detecting part 70.

FIG. 4 shows an example of simultaneous qualitative analysis of twelve kinds of heavy metals (100 ppm) using the qualitative and quantitative analysis device 1 of FIG. 1. Qualitative analysis may be performed on the heavy metals contained in the sample using the color resulted from the color reaction in the detecting part 70. For example, the color of the color reaction can be visually observed to identify the heavy metal contained in the fluid sample.

The detecting part 70 is coated with a chelating agent that reacts with the heavy metal in the sample. The reaction between the heavy metal and the chelating agent is described in Table 2.

TABLE 2

| Metal ion | Chelating agent | Reaction color | Spreading distance | Concentration (ppm) | pH of sample for optimizing reaction |
|---|---|---|---|---|---|
| $Fe^{2+}$ | Bphen (10 mM) | Red | 4 | 850 | pH 4~5 |
| $Ni^{2+}$ | DGM (10 mM) | Pink | 2 | 500 | pH 9~10 |
| $Cu^{2+}$ | DTO (10 mM) | Dark green | 0.8 | 150 | pH 4~5 |
| $Cr^{6+}$ | DPC (10 mM) | Deep purple | 5 | 1000 | pH 2 |
| $Hg^{2+}$ | DTZ (10 mM) | Brown | 2.5 | 500 | pH 9 |
| $As^{2+}$ | EBT (10 mM) | Blue-purple | 5 | 1000 | pH 7 |
| $Zn^{2+}$ | PAN (10 mM) | Magenta | 4.5 | 950 | pH 9 |
| $Mn^{2+}$ | DPC (10 mM) | Deep purple | 4 | 750 | pH 9 |
| $Cd^{2+}$ | PAN (10 mM) | Red | 4.5 | 850 | pH 9 |
| $Pb^{2+}$ | DPC (10 mM) | Pink | 4 | 800 | pH 9 |
| $Co^{2+}$ | PAN (10 mM) | Green | 4.5 | 950 | pH 9 |
| $Ag^{+}$ | DPC (10 mM) | Dark green | — | — | pH 7 |

In the above, Bphen is an abbreviation of bathophenanthroline, DMG is an abbreviation of dimethylglyoxime, DTO is an abbreviation of dithiooxamide, DPC is an abbreviation of diphenylcarbazide, DTZ is an abbreviation of dithizone, EBT is an abbreviation of eriochrome black t, PAN is an abbreviation of 1-(2-pyridylazo)-2-naphthol. The detecting part 70 is made of a porous hydrophilic material, for example, a paper, nitro cellulose, cotton, or a silica-based sol-gel matrix, preferably paper. In addition, the degree of spreading of the fluid sample containing the heavy metal on the detecting part 70 can be quantitatively analyzed using the ruler 80. Referring to the example of FIG. 4, it can be seen that the degree of spreading of the fluid sample containing the heavy metal on the plurality of detecting parts 70 is different.

The ruler 80 is positioned in parallel with the detecting part 70 in the vicinity of the detecting part 70. The ruler 80 may be scaled by, for example, millimeters (mm). Alternatively, in addition to length unit such as mm, the ruler 80 may be scaled by concentration unit such as ppm, ppb and the like. When the ruler 80 is scaled by concentration unit, it may be expressed in terms of the concentration unit obtained from the calibration curve by substituting the spreading length of the heavy metal. For reference, calibration curves of $Co^{2+}$, $Zn^{2+}$, $Hg^{2+}$, $Fe^{2+}$, and $Ni^{2+}$ are shown by way of example in FIGS. 5a to 5e. The quantitative analysis can be performed by measuring the degree of spreading on the detecting part 70 with the ruler 80 and then substituting it in the calibration curve of the corresponding heavy metal ion to obtain the concentration on the x axis corresponding to the degree of spreading on the y axis of the calibration curve.

In addition, the qualitative and quantitative analysis device 1 comprises an air circulation channel 90. The air circulation channel 90 connects the reservoir region 60 and the other end of the detecting part 70. The introduction of an air circulation channel 90 allows the sample to repel air that has been filled in the channel (i.e., sample distribution channel 30, pH adjusting part 50, reservoir region 60, and the like), facilitating the migration of the fluid sample. In addition, it prevents the moisture condensation phenomenon in the detecting part 70, while increasing the evaporation rate of the fluid sample of the detecting part 70. Meanwhile, by centrifugal force, the sample in the reservoir region 60 moves to the detecting part 70 but does not move to the air circulation channel 90. Additionally, in preparation for the possibility of movement, a capillary valve using air pressure is formed by punching a hole having a thickness of about 1 mm and a diameter of about 0.8 mm at the point where the reservoir region 60 and the air circulation channel 90 are connected. Thereby, it is possible to prevent migration from the reservoir region 60 to the air circulation channel 90.

Referring again to FIG. 3, according to the qualitative and quantitative analysis device 1 of the present invention, the rotation of the qualitative and quantitative analysis device 1 may be controlled so that a fluid sample containing heavy metals can be moved from the main injection part 10, to the passage part 20, to the sample distribution channel 30, to the pH adjusting part 50, to the reservoir region 60, and to the detecting part 70. For example, when a fluid sample containing heavy metals is injected into the main injection part 10 and then the qualitative and quantitative analysis device 1 is rotated firstly at 1000 RPM for 30 seconds, the fluid sample containing heavy metals moves from the main injection part 10 through the main passage part 20 to each of the sample distribution channels 30. After stopping, when the qualitative and quantitative analysis device 1 again rotates secondly at 1000 RPM for 30 seconds, the on/off valve 40 is opened by the rotational force so that the sample in the sample distribution channel 30 moves through the pH adjusting part 50 to the reservoir region 60. At this time, the sample is adjusted to have the pH of the microbeads filled in the pH adjusting part 50 while passing through the pH adjusting part 50. When the rotation of the qualitative and quantitative analysis device 1 is stopped, the fluid sample containing the heavy metal is spread from the reservoir region 60 onto the detecting part 70 by the capillary force.

FIG. 6 shows a qualitative and quantitative analysis system 100 in which the qualitative and quantitative analysis device 1 can be mounted and rotated.

Experimental Example for Microbeads

Table 3 shows the pH change of the sample after passing the sample of pH 7.7 through the chamber filled with the microbeads. The amount of sample injected is 2 ml, and the amount of microbeads filled in the chamber is 100 mg.

The pH values in Table 3 are the results measured with S220 SevenCompact™ pH/Ion (METTLER TOLEDO).

TABLE 3

| | | Manufacturing temperature of beads | | | | | | | |
|---|---|---|---|---|---|---|---|---|---|
| | | R.T. | | 50° C. | | 70° C. | | 90° C. | |
| pH of beads | pH of sample before passing through beads | pH of sample after passing through beads | Deviation | pH of sample after passing through beads | Deviation | pH of sample after passing through beads | Deviation | pH of sample after passing through beads | Deviation |
| 1 | 7.7 | 3.7 | −2.7 | 2.5 | −1.5 | 7.1 | −6.1 | 8.2 | −7.2 |
| 2 | 7.7 | 1.1 | 0.9 | 2.6 | −0.6 | 2.0 | 0.0 | 2.9 | −0.9 |
| 3 | 7.7 | 2.1 | 0.9 | 3.5 | −0.5 | 2.7 | 0.3 | 3.0 | 0.0 |
| 4 | 7.7 | 3.8 | 0.2 | 4.7 | −0.7 | 5.0 | −1.0 | 3.1 | 0.9 |
| 5 | 7.7 | 6.8 | −1.8 | 5.5 | −0.5 | 5.5 | −0.5 | 6.9 | −1.9 |
| 6 | 7.7 | 6.0 | 0.0 | 5.9 | 0.1 | 6.0 | 0.0 | 6.0 | 0.0 |
| 7 | 7.7 | 7.1 | −0.1 | 7.0 | 0.0 | 6.9 | 0.1 | 7.1 | −0.1 |
| 8 | 7.7 | 8.2 | −0.2 | 7.9 | 0.1 | 8.1 | −0.1 | 8.2 | −0.2 |
| 9 | 7.7 | 8.0 | 1.0 | 8.9 | 0.1 | 8.9 | 0.1 | 9.0 | 0.0 |
| 10 | 7.7 | 8.9 | 1.1 | 9.9 | 0.1 | 8.3 | 1.7 | 9.4 | 0.6 |
| 11 | 7.7 | 9.7 | 1.3 | 10.7 | 0.3 | — | | | |
| 12 | 7.7 | 10.8 | 1.2 | 10.8 | 1.2 | 11.3 | 0.7 | 11.4 | 0.6 |
| 13 | 7.7 | 11.7 | 1.3 | 11.7 | 1.3 | 11.4 | 1.6 | 12.4 | 0.6 |

FIG. 7 is a graph showing results in Table 3. According to the results of experiment of microbeads depending on manufacturing temperature, it can be seen that when the microbeads were manufactured at 50° C., pH deviation between pH of the sample after passing through the microbeads and pH of the microbeads was the smallest. As the pH of the microbeads increases, conditions under which the correlation of the pH of the sample after passing through the microbeads is constant may be set as optimum conditions.

Referring to the experimental results of Table 3, the optimum temperature condition of production of the microbeads is 50° C. In the case of pH 1 and pH 13, reagents are volatilized during manufacturing the microbeads, causing pH deviation.

In summary, according to the qualitative and quantitative analysis device 1 according to an embodiment of the present invention, it is possible to move the fluid containing heavy metals to the detecting part 70 by the centrifugal force generated due to the rotation of the qualitative and quantitative analysis device 1 to perform qualitative analysis using the color reaction. In addition, it is possible to perform quantitative analysis by confirming the length of the color development region with the patterned ruler 80 in the qualitative and quantitative analysis device 1 by spreading the fluid by the paper capillary force when the rotation is stopped.

In addition, according to the qualitative and quantitative analysis device 1 according to an embodiment of the present invention, since the sample injected into one main injection part 10 is simultaneously spread to the plurality of detecting parts 70 which are radially disposed, it is possible to perform simultaneous qualitative and quantitative analysis of the plurality of heavy metals.

In addition, according to the qualitative and quantitative analysis device 1 according to an embodiment of the present invention, it is possible to improve detection limit of heavy metal ions by control of the rotational force. Specifically, when the spreading speed of the heavy metal-containing sample by the capillary force is faster than the rate of reaction between the heavy metal and the chelating agent on the detecting part, the heavy metal-containing sample is spread throughout the detecting part without sufficient proceeding of the color reaction with the chelating agent. In the case of a heavy metal sample with high concentration, as color development appears, there is no problem for detection, but there is a possibility that the quantitative is deteriorated. In the case of a heavy metal sample with low concentration, as it does not sufficiently react with the chelating agent in the detecting part, color development does not appear, causing to lower the detection sensitivity and the detection limit. However, according to the present invention, since the centrifugal force acts in the opposite direction to the capillary force, it is applied to control the spreading speed of the solution by the capillary force, so that the color reaction can be sufficiently performed on the detecting part to increase the detection limit.

In addition, according to the qualitative and quantitative analysis device 1 according to an embodiment of the present invention, it is possible to achieve economical and rapid qualitative/quantitative analysis of multiple heavy metals. It is more economical and reduces the time required for analysis, compared to conventional expensive spectroscopic or mass spectrometry-based detecting device of heavy metals. In addition, it is possible to be applied quickly and conveniently in the field requiring qualitative/quantitative analysis of heavy metals.

In addition, according to the qualitative and quantitative analysis device 1 according to an embodiment of the present invention, the sample is adjusted to have a pH that is optimized to occur the reaction between the heavy metal and the chelating agent in the detecting part 70 while passing through the microbeads filled in the pH adjusting part 50, before the sample is spread in the detecting part 70.

It will be appreciated that the technical configuration of the present invention described above may be embodied in other specific forms by those skilled in the art without changing the technical spirit or essential features of the present invention. Therefore, it is to be understood that the embodiments described above are exemplary in all respects and not restrictive. In addition, the scope of the present invention is indicated by the appended claims to be described later rather than the detailed description above. In addition, it should be construed that all changes or modifications derived from the meaning and scope of the claims and equivalent concepts thereof are included in the scope of the present invention.

INDUSTRIAL AVAILABILITY

According to the qualitative and quantitative analysis device according to one embodiment of the present invention, it is possible to increase detection limit of heavy metals by automated control of fluid and by adjusting rotational force and capillary force. It is possible to improve detection limit of heavy metal ions by control of rotational force. That is, it is possible to improve detection limit by adjusting color reaction time and color development area by adjusting centrifugal force and capillary force by control of rotation.

In addition, according to the qualitative and quantitative analysis device according to an embodiment of the present invention, qualitative analysis and quantitative analysis of a plurality of heavy metals can be performed in a single device. According to the present invention, it is possible to achieve economical and rapid qualitative/quantitative analysis of multiple heavy metals. It is more economical and can reduce the time required for analysis, compared to conventional expensive spectroscopic or mass spectrometry-based detecting device of heavy metals. In addition, the configuration for qualitative analysis and the configuration for quantitative analysis are integrated into one miniaturized device, which can be quickly and conveniently applied in the field requiring qualitative/quantitative analysis of heavy metals.

In addition, since each component such as a pH adjusting part, a detecting part, and the like are patterned in one device, it is easy to manufacture a qualitative and quantitative analysis device.

In addition, according to the qualitative and quantitative analysis device according to an embodiment of the present invention, by providing an air circulation channel, it is possible to prevent moisture condensation of the detecting part when the fluid sample is spread in the detecting part so that color development can be easily identified and errors of analysis can be minimized, and it is possible to move a fluid sample more uniformly when the fluid sample is spread in the detecting part so that color reaction between chelating agent coated one the detecting part and heavy metals of the sample can more uniformly occur.

What is claimed is:

1. A rotary platform device for qualitative and quantitative analysis comprising:
    a main injection part positioned near a rotating shaft of a rotary platform, wherein the main injection part is configured to receive a fluid sample containing heavy metals;
    a pH adjusting part configured for adjusting pH of the fluid sample;
    a detecting part coated with a chelating agent configured to initiate a color reaction with the heavy metals in the fluid sample by spreading a pH-adjusted fluid sample; and
    a ruler configured for measuring a spreading distance of the color reaction;

wherein the rotating shaft and the rotary platform are configured so that the fluid sample moves from the main injection part through the pH adjusting part to the detecting part by a rotation of the rotating shaft and the rotary platform, and wherein the pH adjusting part is filled with microbeads and a surface of the microbeads is coated with a salt configured to adjust a pH of the fluid sample.

2. The rotary platform device for qualitative and quantitative analysis according to claim 1, further comprising:

a reservoir region connecting the pH adjusting part to the detecting part, wherein one end of the detecting part is accommodated in the reservoir region.

3. The rotary platform device for qualitative and quantitative analysis according to claim 2, wherein the pH adjusting part, the detecting part, the reservoir region, and the ruler are provided in plurality, and each of the pH adjusting parts, each of the detecting parts, each of the reservoir regions, and each of the rulers are radially and symmetrically disposed on the rotary platform.

4. The rotary platform device for qualitative and quantitative analysis according to claim 3, further comprising:

a main passage part connected to an end of the main injection part; and a plurality of sample distribution channels connected to the main passage part, wherein each of the sample distribution channels extends outward from and is disposed radially and symmetrically from the main passage part.

5. The rotary platform device for qualitative and quantitative analysis according to claim 4, wherein the main injection part comprises a sample reservoir for storing the fluid sample before distributing to each of the sample distribution channels, and the sample reservoir and the main passage part have a spiral shape.

6. The rotary platform device for qualitative and quantitative analysis according to claim 5, further comprising:

a plurality of on/off valves, wherein each of the on/off valves is disposed between each of the sample distribution channels and each of the pH adjusting parts, and the each of the on/off valves is configured to open by a rotational force of the rotary platform to allow the fluid sample in the each of the sample distribution channels to pass through the each of the pH adjusting parts.

7. The rotary platform device for qualitative and quantitative analysis according to claim 6, further comprising a plurality of air circulation channels, wherein each of the air circulation channels connects the each of the reservoir regions and each other end of the each of the detecting parts, and each of the air circulation channels are configured to increase an evaporation rate of the fluid sample in the each of the detecting parts and prevent moisture condensation in the each of the detecting parts.

8. The rotary platform device for qualitative and quantitative analysis according to claim 7, wherein the rotary platform comprises:

a top layer including the main injection part, the main passage part, each sample distribution channel, each on/off valve, each pH adjusting part and each reservoir region;

a middle layer including each air circulation channel and each reservoir region, the middle layer having an opening configured to expose a portion of each detecting part; and a bottom layer including each reservoir region and each ruler, the bottom layer having a space in which each detecting part is inserted.

9. The rotary platform device for qualitative and quantitative analysis according to claim 2, wherein the rotation of the rotating shaft and the rotary platform are controlled by a method comprising:

firstly rotating and then stopping the rotating shaft and the rotary platform so that the fluid sample injected into the main injection part moves to a sample distribution channel;

secondly rotating the rotating shaft and the rotary platform so that the fluid sample moved to the sample distribution channel moves through the pH adjusting part to the reservoir region; and stopping the rotating shaft and the rotary platform so that the fluid sample moved to the reservoir region spreads into the detecting part.

10. The rotary platform device for qualitative and quantitative analysis according to claim 9, wherein the first rotation and the second rotation are performed at a rotation rate of 1000 RPM for 30 seconds, respectively.

11. The rotary platform device for qualitative and quantitative analysis according to claim 1, wherein the fluid sample is adjusted to have a pH to initiate the color reaction between the heavy metals contained in the fluid sample and the chelating agent while passing through microbeads filled in the pH adjusting part.

12. The rotary platform device for qualitative and quantitative analysis according to claim 1, wherein the heavy metals contained in the fluid sample are $Fe^{2+}$, $Ni^{2+}$, $Cu^{2+}$, $Cr^{6+}$, $Hg^{2+}$, $As^{2+}$, $Zn^{2+}$, $Mn^{2+}$, $Cd^{2+}$, $Pb^{2+}$, $Co^{2+}$, or $Ag^{+}$.

13. The rotary platform device for qualitative and quantitative analysis according to claim 1, wherein the chelating agent coated on the detecting part comprises bathophenanthroline (Bphen), dimethylglyoxime (DMG), dithiooxamide (DTO), diphenylcarbazide (DPC), dithizone (DTZ), Eriochrome Black T (EBT), or 1-(2-pyridylazo)-2-naphthol (PAN).

14. A method for detecting heavy metals by using the rotary platform device for qualitative and quantitative analysis of claim 1, comprising:

performing a quantitative analysis by the color reaction of the heavy metals in the detecting part, and performing a qualitative analysis by measuring the spreading distance of the color reaction.

\* \* \* \* \*